(12) United States Patent
Krause

(10) Patent No.: US 12,274,792 B2
(45) Date of Patent: Apr. 15, 2025

(54) METHOD FOR AUTOMATICALLY PRODUCING INDIVIDUALIZED TABLETS, AND TABLET PRESS FOR AUTOMATICALLY PRODUCING INDIVIDUALIZED TABLETS

(71) Applicant: PrivMed X AB, Akersberga (SE)

(72) Inventor: Ingo Krause, Scharbeutz (DE)

(73) Assignee: PrivMed X AB, Akersberga (SE)

( * ) Notice: Subject to any disclaimer, the term of this patent is extended or adjusted under 35 U.S.C. 154(b) by 889 days.

(21) Appl. No.: 17/316,857

(22) Filed: May 11, 2021

(65) Prior Publication Data
US 2021/0267905 A1    Sep. 2, 2021

Related U.S. Application Data

(63) Continuation of application No. PCT/EP2019/080994, filed on Nov. 12, 2019.

(30) Foreign Application Priority Data

Nov. 12, 2018 (EP) ..................................... 18205665

(51) Int. Cl.
| | | |
|---|---|---|
| *A61K 9/20* | (2006.01) | |
| *A61J 3/06* | (2006.01) | |
| *B30B 11/00* | (2006.01) | |
| *B30B 11/02* | (2006.01) | |
| *B30B 11/04* | (2006.01) | |
| *B30B 15/02* | (2006.01) | |
| *B30B 15/26* | (2006.01) | |

(52) U.S. Cl.
CPC .............. *A61K 9/2095* (2013.01); *A61J 3/06* (2013.01); *B30B 11/005* (2013.01); *B30B 11/025* (2013.01); *B30B 11/04* (2013.01); *B30B 15/028* (2013.01); *B30B 15/26* (2013.01)

(58) Field of Classification Search
CPC ........ A61K 9/2095; A61J 3/06; B30B 11/005; B30B 11/025; B30B 11/04; B30B 15/028; B30B 15/26
See application file for complete search history.

(56) References Cited

U.S. PATENT DOCUMENTS

| | | | |
|---|---|---|---|
| 2011/0068511 A1* | 3/2011 | Sowden ............... | A61K 9/2086 264/449 |
| 2015/0317586 A1 | 11/2015 | Kassman | |
| 2015/0374586 A1* | 12/2015 | Gamlen .................. | B30B 11/14 425/150 |
| 2018/0221245 A1 | 8/2018 | Gamlen | |

FOREIGN PATENT DOCUMENTS

| | | | | |
|---|---|---|---|---|
| CN | 206170705 U | * | 5/2017 | |
| DE | 102013211305 A1 | * | 12/2014 | ............ B30B 11/10 |
| EP | 2823958 A2 | | 1/2015 | |
| EP | 2977195 A1 | | 1/2016 | |
| WO | WO-2017068375 A1 | * | 4/2017 | ................ A61J 3/10 |

OTHER PUBLICATIONS

Machine translation of CN206170705U (Year: 2017).*
Pitt et al.; Tabletting (Chapter 16); Science Direct; Handbook of Powder Technology vol. 11, 2007, pp. 735-778. (Year: 2007).*
Machine translation of DE102013211305A1 (Year: 2014).*
International Search Report dated Feb. 21, 2020 issued in PCT/EP2019/080994.

* cited by examiner

*Primary Examiner* — Robert A Wax
*Assistant Examiner* — John W Lippert, III
(74) *Attorney, Agent, or Firm* — Scully, Scott, Murphy & Presser, P.C.

(57) ABSTRACT

A tablet press for producing tablets including: a press chamber, a receiving chamber, a first material container having the first active substance with a first dosing device, a controller, and an input device. The press chamber has an extendable upper punch, an extendable lower punch, and a die. The input device inputs a target indicating a number of produced tablets and a target mass indicating a quantity of the first active substance and transmits the target number and the target mass to the controller. The controller actuates the first dosing device, the upper punch, and the lower punch such that a quantity of the first active substance that corresponds to the target mass is filled into a central opening of the die and pressed by the punches to form a tablet, and to repeat until the target number of tablets are produced.

19 Claims, 5 Drawing Sheets

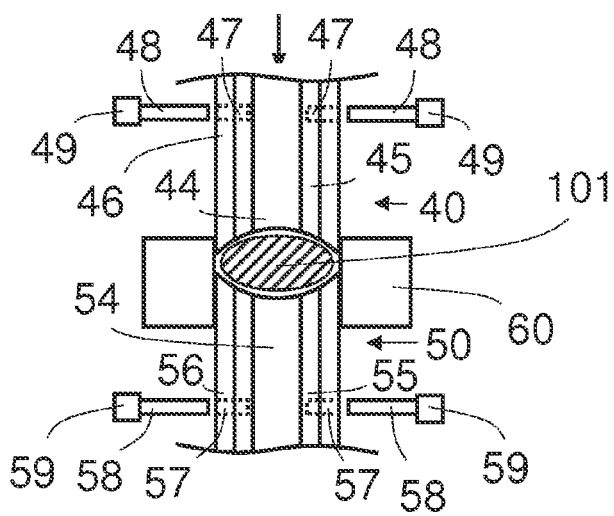
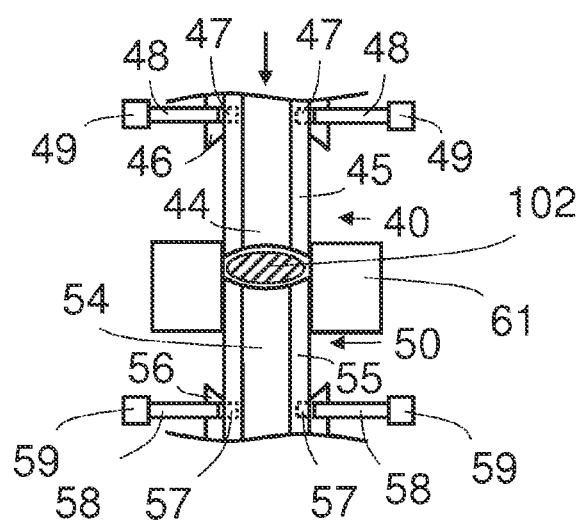
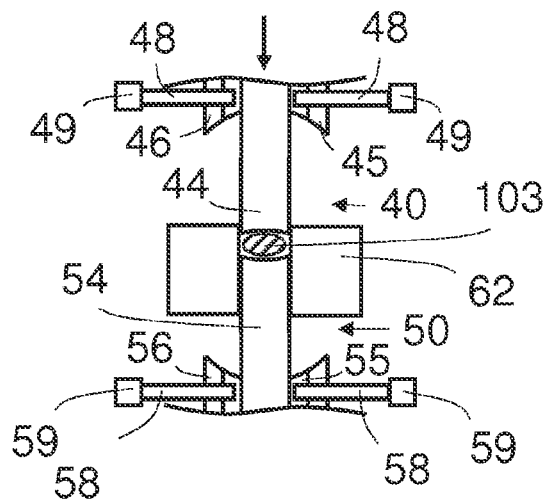

METHOD FOR AUTOMATICALLY
PRODUCING INDIVIDUALIZED TABLETS,
AND TABLET PRESS FOR
AUTOMATICALLY PRODUCING
INDIVIDUALIZED TABLETS

CROSS-REFERENCE TO RELATED
APPLICATION

The present application is a continuation of PCT/EP2019/080994 filed on Nov. 12, 2019, which is based upon and claims the benefit to EP 18205665.5 filed on Nov. 12, 2018, the entire contents of each of which are incorporated herein by reference.

BACKGROUND

Field

The present disclosure relates to a method for automatically producing a specifiable number of individualized tablets with a specifiable quantity of a first active substance by means of a tablet press.

The present disclosure also relates to a tablet press for automatically producing a specifiable number of individualized tablets with a specifiable quantity of a first active substance.

Prior Art

Tablets play an indispensable role in medical and non-medical fields today, from the administration of medications to dietary supplements.

To produce tablets, a die with a central opening is frequently used, into which the active substance from which the tablet is to be produced is filled. By means of a lower punch and an upper punch, the active substance in the central opening is pressed in order to form a tablet.

To meet the great need for tablets, the tablets are frequently produced in standardized sizes with a defined quantity of active substance. For this purpose, rotary presses, for example, are used which comprise up to a hundred dies and punch pairs, which are driven in a rotating and synchronized manner by means of a rotating plate. Such rotary presses can produce up to 1.6 million tablets per hour.

However, especially in medical applications, the active substance quantities to be administered are dependent on the individual patients, the absorption capacity of the active substance, and the current state of health of these patients. Especially, but not only, children and older people require a specially tailored adjustment of the dose.

Since common medical preparations of active substances are usually only available in a number of standard doses, doctors and pharmacists almost always have to select a dose that is too high, since a dose that is too low would not have the desired treatment effect. However, doses that are too high unnecessarily strain the patients' organ system and lead to damage in the long term. Splitting tablets into smaller pieces by means of a knife is not feasible or practical for patients.

In addition, tablets are frequently sold in tablet packages with a specified number of tablets. This leads to waste of raw pharmaceutical materials and extra tablets that are not needed by the patient and are thrown away.

SUMMARY

An object is to simplify dosing and intake of active substances administered in tablet form that is individualized for patients.

Such object can be solved by a method for automatically producing a specifiable number of individualized tablets with a specifiable quantity of a first active substance by means of a tablet press, which may be compact, the method comprising:

inputting a target number which indicates the number of tablets to be produced and a target mass which indicates the quantity of the first active substance per tablet into an input device of the tablet press, transmitting the target number and the target mass from the input device to a control system of the tablet press, wherein the control system controls a first dosing device of a first material container, a vertically extendable upper punch, and a vertically extendable lower punch, filling a quantity of the first active substance which corresponds to the target mass from the first material container into a central opening of a die by means of the first dosing device, wherein a pressure face of the lower punch, the outer circumference of which corresponds to an inner circumference of the central opening, closes the central opening from below, pressing the first active substance by vertically extending a pressure face of the upper punch, the outer circumference of which corresponds to the inner circumference of the central opening, into the central opening from above, releasing a pressed tablet from the die by retracting the pressure face of the upper punch and vertically extending a pressure face of the lower punch through the central opening from below, transferring the pressed tablet into the tablet container by means of the transfer device, and repeating the filling of the quantity of the first active substance, pressing the first active substance, and releasing the pressed tablet until the number of pressed tablets corresponds to the target number.

A tablet container can be arranged in a receiving chamber of the tablet press before the method and transferred into the tablet container after the release of the pressed tablet by means of a transfer device controlled by the control system.

This method can provide the patient with a specifiable target number of individualized tablets with a specifiable target mass of the first active substance. The target mass can be defined by a doctor or a pharmacist, taking into account the state of health and the physical characteristics of the patient, such as, for example, his body weight. Since the active substance contained in the tablet corresponds exactly to the target mass, splitting the tablet is unnecessary. In this manner, doses that are too high are advantageously avoided and taking the tablets is made easier for the patient.

The target number can also be defined by the doctor or the pharmacist. In doing so, how quickly the state of health of the patient changes and how often an adjustment of the dose is required can also be taken into account. The target number can be chosen such that the produced tablets are sufficient for treating the patient until the next diagnosis without excess tablets being produced. Wasting tablets by issuing standardized tablet packages that contain more than the required tablets is advantageously avoided.

The tablet press can be compact. This can be achieved in that the tablet press comprises only a single upper punch and/or a single lower punch. The tablet press can be located in a doctor's office, a pharmacy, or at the patient's home. The tablets can be produced immediately after the determination of the target mass and target number in the doctor's office, in the pharmacy, or by the patient himself at home. A decentralized method for producing individualized tablets outside of industrial production facilities is thus provided. Since the number of the individualized tablets required by a patient is relatively small, high production speed is not necessary for their production. Instead, a plurality of tablet presses in a plurality of doctor's offices, pharmacies, or patient dwellings can meet the patients' needs for individualized tablets.

The first material container can be releasably fixed to a first dosing opening, such as a press chamber, of the tablet press. This enables the first material container to be quickly changed, for example when tablets with a different active substance are to be produced. The first dosing device can be a component of the first material container and forms a unit therewith. The first active substance can be either a single active substance or a mixture of different active substances.

The pressure face of the lower punch can close the central opening from below in that the pressure face of the lower punch can be pushed into the central opening from below. This creates a trough, the walls of which are formed by the central opening and the bottom of which is formed by the pressure face of the lower punch. To release the pressed tablet, the pressure face of the lower punch is extended further upwards until it is in particular level with the upper edge of the die.

The input device can comprise input means for inputting the target mass and the target number, such as a touchscreen. The input device can be configured to display the input target number and/or the input target mass and/or additional information, such as patient information and/or information about the first active substance, on a data display. The input device can further comprise an input means with which the production of the tablets is started. The input device can comprise a security access system. For example, the input device can be secured by means of an access code or comprise a fingerprint scanner.

The target number and the target mass can be coded in an identifier, such as a barcode, which can be printed onto a prescription which is issued to the patient. The identifier can be read by means of an image capture device of the input device, such as a camera, and transmitted to the control system, wherein the control system determines the target number and the target mass from the identifier.

The control system can be a computer configured to read out the target mass and target number input into the input device and actuate the first dosing device, the upper punch, the lower punch, and the transfer device.

The transfer device can comprise a pushing device, by means of which the produced tablet is pushed down by the pressure face of the lower punch. The transfer device can further comprise a channel that opens above a tablet container arranged in the receiving chamber. The tablets pushed down by the pressure face of the lower punch fall through the channel into the tablet container Immediately after the transfer of the pressed tablet, the next tablet is produced until the target number is reached.

The control system can calculate a filling volume and thus a target circumference, taking into account the target mass, and if necessary a bulk density, of the first active substance, select a target die from at least two dies arranged in the tablet press with different inner circumferences, the inner circumference of the target die's central opening corresponding to the target circumference, and actuate a first positioning device such that the target die is arranged above the lower punch, wherein the first positioning device can be a first rotary disk with a vertical axis of rotation arranged between the upper punch and the lower punch, on which the at least two dies arranged in the tablet press are arranged, such as by being fixed.

The size of the pressed tablets can be varied in this manner. To do this, the control system can automatically determine a filling volume and thus an appropriate target circumference using the target mass, and if necessary, the bulk density, of the first active substance, select an appropriate target die, and arrange it above the lower punch. Manually changing the die is thus unnecessary. The variability of the size of the pressed tablets enables individualized tablets with very different active substance quantities to be produced.

At least three dies with different inner circumferences of their central openings can be fixed to the rotary disk.

The outer circumference of the pressure face of the upper punch for pressing the first active substance can be adapted to the inner circumference of the die in that a number of vertically telescoping upper punch shafts of the upper punch arranged inside each other are extended downwards, wherein the outer circumference of the outer extended upper punch shaft corresponds to the inner circumference of the die.

By adapting the outer circumference of the pressure face of the upper punch to the inner circumference of the die, replacing the upper punch when using dies with different inner circumferences becomes unnecessary. The outer circumference of the pressure face of the upper punch is adapted by extending the upper punch shafts. The pressure face of the upper punch corresponds to the entirety of the pressure faces of the extended upper punch shafts. The pressure faces of the upper punch shafts can be formed such that the pressure face of the upper punch is always continuous.

For each die arranged on the first rotary disk, the upper punch can comprise an associated upper punch shaft, the cross-sectional shape of which corresponds to the cross-sectional shape of the central opening of one of the dies. The upper punch shaft associated with the central opening and all upper punch shafts arranged farther inwards can always extended to press the first active substance. The upper punch shafts can be substantially arranged inside each other basically without gaps. In this manner, the pressure face of the upper punch is always free of grooves, such that tablets with a smooth surface are produced.

The outer circumference of the pressure face of the lower punch can be adapted to the inner circumference of the die before the filling of the quantity of the first active substance in that a number of vertically telescoping lower punch shafts of the lower punch arranged inside each other are extended upwards, wherein the outer circumference of the outer extended lower punch shaft corresponds to the inner circumference of the die.

By adapting the outer circumference of the pressure face of the lower punch to the inner circumference of the dies, replacing the lower punch when using dies with different inner circumferences also becomes unnecessary. The outer circumference of the pressure face of the lower punch can be adapted to the inner circumference of the dies before the pressure face of the lower punch is extended into the central opening from below in order to close it from below.

The lower punch shafts can be made as a mirror image to the upper punch shafts such that the advantages and characteristics described with regard to the upper punch shafts also apply to the lower punch shafts.

The mass of the first active substance filled into the central opening can be measured in that, during the filling, the total mass of the first material container can be determined by means of a scale and from this the quantity of the first active substance taken from the first material container can be calculated.

In other words, the mass of the filled first active substance can be determined by means of a difference measurement of the remaining mass of the first material container. This allows a precise measurement of the filled first active substance, since a measurement in the press chamber, which is susceptible to vibrations, is unnecessary.

The first dosing device can be arranged vertically above the central opening by means of a second positioning device during the filling of the quantity of the first active substance, wherein the upper punch is arranged vertically above the central opening by means of the second positioning device after the filling of the quantity of the first active substance and before the pressing of the first active substance, wherein the second positioning device can be a second rotary disk with a vertical axis of rotation, on which the first dosing device and the upper punch are arranged, such as by being fixed.

The second positioning device can simplify the filling of the first active substance. By arranging the first dosing device above the central opening, the filling of the first active substance can take place from above directly and without losses. After the filling of the first active substance, the first dosing device can be moved to the side such that the upper punch is arranged above the central opening.

Such object can be further solved by a method for producing a specifiable number of individualized two-layer tablets with a specifiable quantity of the first active substance and a specifiable quantity of a second active substance, wherein the above method additionally comprises:

inputting a second-layer target mass into the input device and transmitting the second-layer target mass to the control system, wherein the second-layer target mass indicates the quantity of the second active substance per two-layer tablet,
  positioning a second dosing device of a second material container above the central opening by means of the second positioning device,
  filling a quantity of a second active substance that corresponds to the second-layer target mass into the central opening by means of the second dosing device,
  positioning the upper punch above the central opening by means of the second positioning device,
  pressing the second active substance by vertically extending the pressure face of the upper punch into the central opening from above,
  wherein, except for inputting the second-layer target mass and transmitting the second-layer target mass, such additional method is carried out after pressing the first active substance and before dispensing the pressed tablet.

Before this method is performed, the second material container, which is filled with the second active substance, can be fixed to a second dosing opening of the tablet press and the second dosing device can be fixed to a free point of the second positioning device. Pressing the first active substance can take place with a lower pressure than pressing the second active substance. In this manner, pressing the first active substance creates a cavity for the second active substance and prevents the two tablet hemispheres from falling apart after the pressing of the second active substance.

This method can enable individualized two-layer tablets to be produced that are adapted to the patient's needs. After a first layer is produced by filling and pressing the first active substance, the second dosing device can be arranged above the central opening by means of the second positioning device and the central opening can be filled with the second-layer target mass of the second active substance. Then, the second active substance can be pressed by means of the upper punch in order to form a second layer on top of the first layer. Then, the produced two-layer tablet can be released from the die in the manner described above and transferred into the tablet container.

Such object can also be solved by a tablet press for automatically producing a specifiable number of individualized tablets with a specifiable quantity of a first active substance, comprising a press chamber, a receiving chamber for receiving a tablet container, a first material container that can be filled with the first active substance and has a first dosing device, a control system, and an input device, wherein the press chamber has a vertically extendable upper punch, a vertically extendable lower punch, and at least one die, wherein the input device comprises input means for inputting a target number that indicates the number of tablets to be produced and a target mass that indicates the quantity of the first active substance per tablet, wherein the input device is configured to transmit the target number and the target mass to the control system, and wherein the control system is configured to actuate the first dosing device, the upper punch, and the lower punch such that a quantity of the first active substance that corresponds to the target mass is filled into a central opening of the die and pressed by means of the upper punch and the lower punch in order to form a tablet, and to repeat this process until the target number of tablets has been produced.

The tablet press embodies the same advantages, features, and characteristics as the previously described method for automatically producing a specifiable number of individualized tablets with a specifiable quantity of a first active substance by means of a tablet press.

The tablet press can represent a decentralized device for producing individualized tablets. The individualized tablets can be produced directly on site, meaning in a doctor's office, a pharmacy, or a pharmaceutical production facility by expert doctors or pharmacists, or by patients who have been trained accordingly. With the individualized tablets, incorrect dosing/doses that are too high are avoided and taking the tablets is made easier for the patient, since they no longer have to be split.

The lower punch can be arranged in a fixed location in the press chamber. The position of the lower punch in the press chamber therefore does not have to change. This enables the pressing force acting on the lower punch to be measured easily.

The tablet press can comprise two dies, the central openings of which have different inner circumferences, wherein the control system is configured to calculate a filling volume and thus a target circumference, taking into account the target mass, and if necessary, a bulk density, of the first active substance, to select a target die from the at least two dies, the inner circumference of the target die's central opening corresponding to the target circumference, and to actuate a first positioning device such that the target die is arranged above the lower punch, wherein the first positioning device can be a first rotary disk with a vertical axis of rotation arranged between the upper punch and the lower punch, on which the at least two dies are arranged, such as by being fixed.

The upper punch can comprise at least two vertically telescoping upper punch shafts arranged inside each other, by means of which an outer circumference of a pressure face of the upper punch can be adapted to the inner circumference of the central opening of the at least one die by individually extending the upper punch shafts.

The lower punch can comprise at least two vertically telescoping lower punch shafts arranged inside each other, by means of which an outer circumference of a pressure face of the lower punch can be adapted to the inner circumference of the central opening of the at least one die by individually extending the lower punch shafts.

The press chamber can comprise a first pushing and pulling device, by means of which at least one upper locking pin can be pushed into a horizontal hole in side walls of the upper punch shafts to vertically fix a definable number of the upper punch shafts, wherein the press chamber can comprise a second pushing and pulling device, by means of which at least one lower locking pin can be pushed into a horizontal hole in side walls of the lower punch shafts to vertically fix a definable number of the lower punch shafts.

By means of the locking pins, only the desired punch shafts can be extended when the upper punch and the lower punch are extended.

The upper punch can be extended by an upper piston that presses on the upper punch from above. The lower punch can be correspondingly extended by a lower piston that presses on the lower punch from below. The upper piston can be connected exclusively to the innermost upper punch shaft and the lower piston can be connected exclusively to the innermost lower punch shaft. If further upper punch shafts and/or lower punch shafts are to be additionally extended, these further upper punch shafts and/or lower punch shafts can be coupled with the inner upper punch shaft and/or lower punch shaft by means of a coupling pin. The coupling pin can be driven by a rod-shaped pushing and pulling device. The pushing and pulling device can be guided in a groove running vertically inside a punch carrier such that it can move in sync with the vertical movement of the extended upper punch shafts and/or lower punch shafts.

The first material container can be coupled with a scale, by means of which the total mass of the first material container can be measured.

A second positioning device can comprise, by means of which the upper punch and the first dosing device, a second dosing device of a second material container, which can be alternately arranged vertically above the central opening of the die arranged above the lower punch, wherein the second positioning device can be a second rotary disk with a vertical axis of rotation, on which the upper punch and the first dosing device, and the second dosing device, are arranged, such as by being fixed.

According to an embodiment, the press chamber can be dust-tight, wherein the receiving chamber can be closed in a dust-tight manner.

Such configuration avoids contamination of the receiving chamber and/or of a tablet container arranged in the receiving chamber and/or of the region outside the tablet press.

The lower punch and/or the upper punch can be coupled with a pressure measuring device, by means of which a pressure acting on the lower punch and/or the upper punch can be measured.

By means of the pressure measuring device, the pressure during production of the tablets can be monitored, a tablet hardness and/or break resistance of the tablets can be controlled, and damage to the punches and/or dies can be prevented.

BRIEF DESCRIPTION OF THE DRAWINGS

Further features will become apparent from the description of embodiments together with the claims and the attached drawings. Embodiments can fulfill individual features or a combination of several features.

The embodiments are described below, without restricting the general idea of the invention, based on exemplary embodiments in reference to the drawings, whereby we expressly refer to the drawings with regard to the disclosure of all details that are not explained in greater detail in the text. In the figures:

FIG. 8a-c illustrate schematically simplified cross-sectional views of an upper punch, a lower punch, and multiple dies during the pressing process of tablets with different active substance quantities.

In the drawings, the same or similar elements and/or parts are always provided with the same reference numbers; a reintroduction will therefore be omitted in each case.

DETAILED DESCRIPTION

Figure 1:
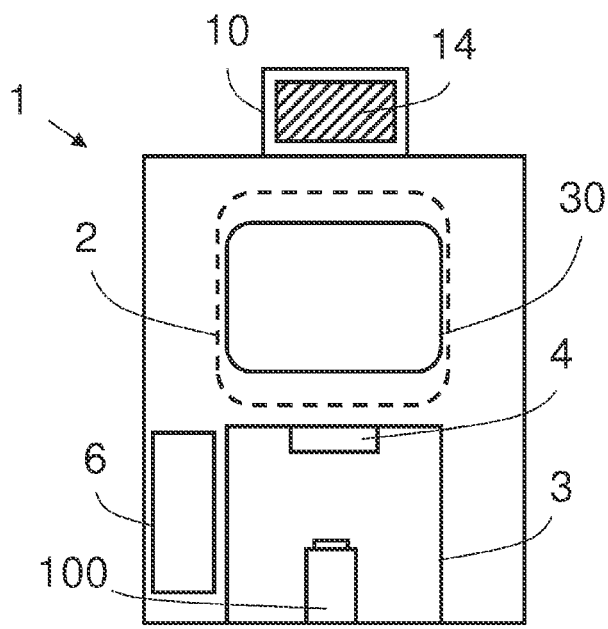
FIG. 1 illustrates a schematically simplified diagram of a tablet press for automatically producing a specifiable number of individualized tablets with a specifiable quantity of a first active substance.

FIG. 1 shows a schematically simplified exemplary embodiment of a tablet press 1. The tablet press 1 comprises a press chamber 2 represented by a dashed line, a first material container 10 releasably fixed to a shell of the tablet press 1 and filled with a first active substance 14, a receiving chamber 3 in which a tablet container 100 can be arranged, a transfer device 4 for transporting the produced tablets from the press chamber 2 into the tablet container 100, a control system 6 for controlling the tablet press 1, and an input device 30 for operating the tablet press 1. The input device 30 can comprises a security access system. For example, the input device 30 can be secured by means of an access code or comprises a fingerprint scanner.

The control system 6 is, for example, a computer that is configured to control the tablet press 1 such that a target number of individualized tablets with a target mass of the first active substance 14 is produced automatically. The receiving chamber 3 can be closed according to an embodiment such that no dust escapes from the tablet press 1 and no contaminants enter the tablet press 1 during the production of the tablets.

Figure 2:
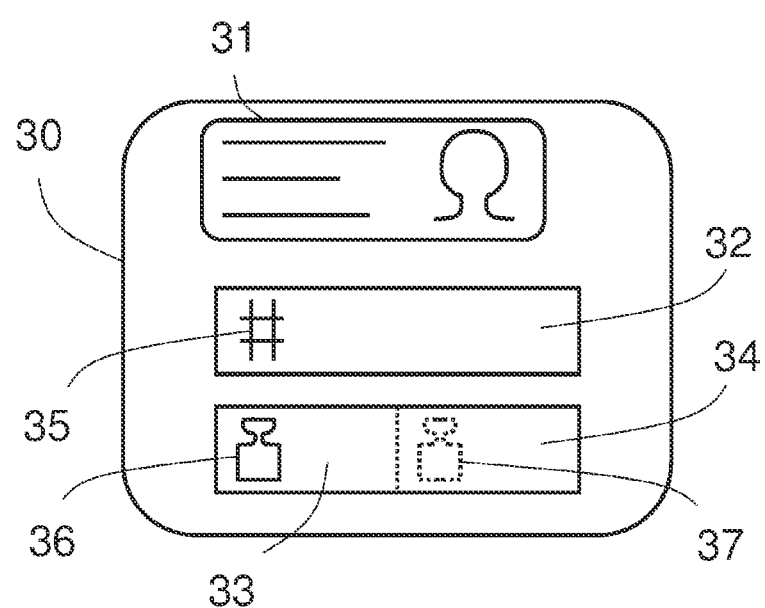
FIG. 2 illustrates a schematically simplified diagram of an input device of the tablet press from FIG. 1.

FIG. 2 shows a schematically simplified detailed view of the input device 30, which is a touchscreen in the embodiment shown. The input device 30 comprises a data display 31, for example a region of the screen, on which information about the first active substance 14 and/or a patient is displayed. The input device 30 further comprises multiple input means 32, 33, 34, which are, for example, additional regions of the screen. By means of the input means 32, 33, 34, the target number 35, the target mass 36, and if necessary, a second-layer target mass 37 can be input. The input values are displayed for verification. In addition, a further input means (not shown) can be provided, with which the production of the tablets can be started.

Figure 3:
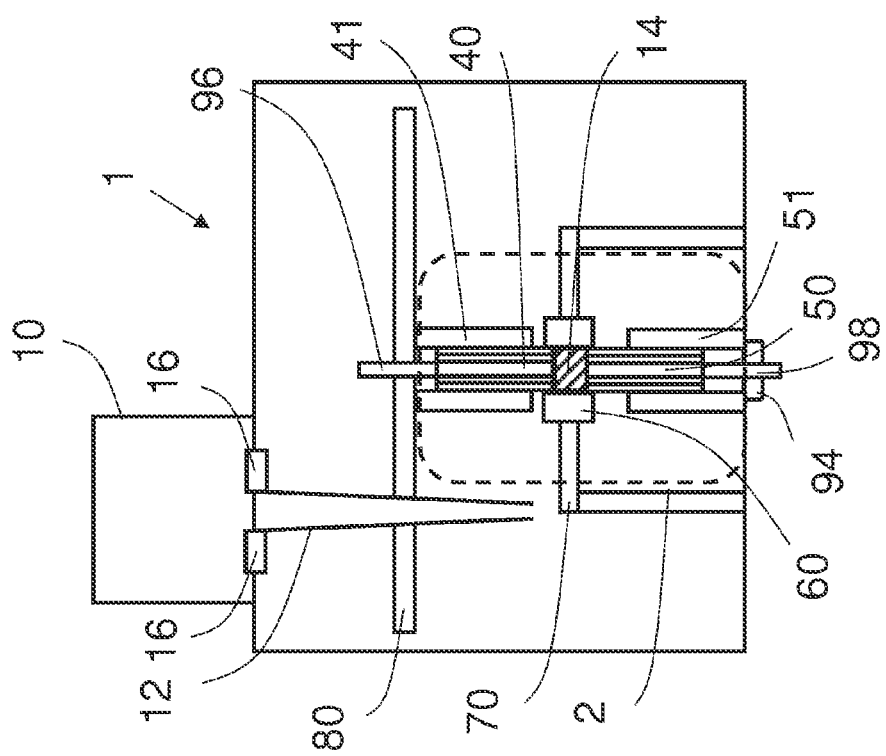
FIG. 3 illustrates a schematically simplified cross-sectional view of a press chamber and a material container of a tablet press during filling of an active substance.

In FIG. 3, a schematically simplified cross-sectional view of the tablet press 1 with the press chamber 2 and the first material container 10 is shown. The first material container 10 comprises a first dosing device 12 for filling the first active substance 14 into the central opening of a die 60. The first dosing device 12 is, for example, a closable funnel. A scale 16 is arranged such that it measures the total mass of the first material container 10. By measuring the difference of the mass of the first material container 10 before and after filling, the mass of the first active substance 14 filled into the die 60 can be determined.

The die 60 is fixed to a first positioning device 70 inside the press chamber 2, which is a rotary disk in the embodiment shown. Further dies (not shown in FIG. 3) can be fixed to this first rotary disk and can be moved into a position above a lower punch 50 by rotating the first rotary disk. To do so, the lower punch 50 is first lowered so that the rotary disk can be rotated.

The lower punch 50 is arranged below the die 60 in the press chamber 2. The lower punch 50 can be extended in the vertical direction by means of a lower piston 98. A lower punch carrier 51 surrounds and supports the lower punch 50. The pressure acting on the lower punch 50 can be measured by means of a pressure measuring device (sensor) 94. Before the first active substance 14 is filled into the die 60, the lower punch 50 is moved into the die 60 from below such that a trough for receiving the first active substance 14 is created.

An upper punch 40 surrounded and supported by an upper punch carrier 41 is also arranged in the press chamber 2.

The upper punch 40 can be extended in the vertical direction by means of an upper piston 96.

The first dosing device 12 and the upper punch 40 are fixed to a second positioning device 80, which is a second rotary disk in the embodiment shown.

To fill the die 60 with the first active substance 14, the second positioning device 80 is actuated by the control system 6 such that the first dosing device 12 is arranged above the lower punch 50 and the die 60, as shown in FIG. 3. Naturally, this only occurs if the first dosing device 12 is not yet arranged above the lower punch 50. Then, the central opening of the die 60 is filled with the first active substance 14 by means of the first dosing device 12 until the target mass 36 is reached. This is monitored with the scale 16.

Figure 4:
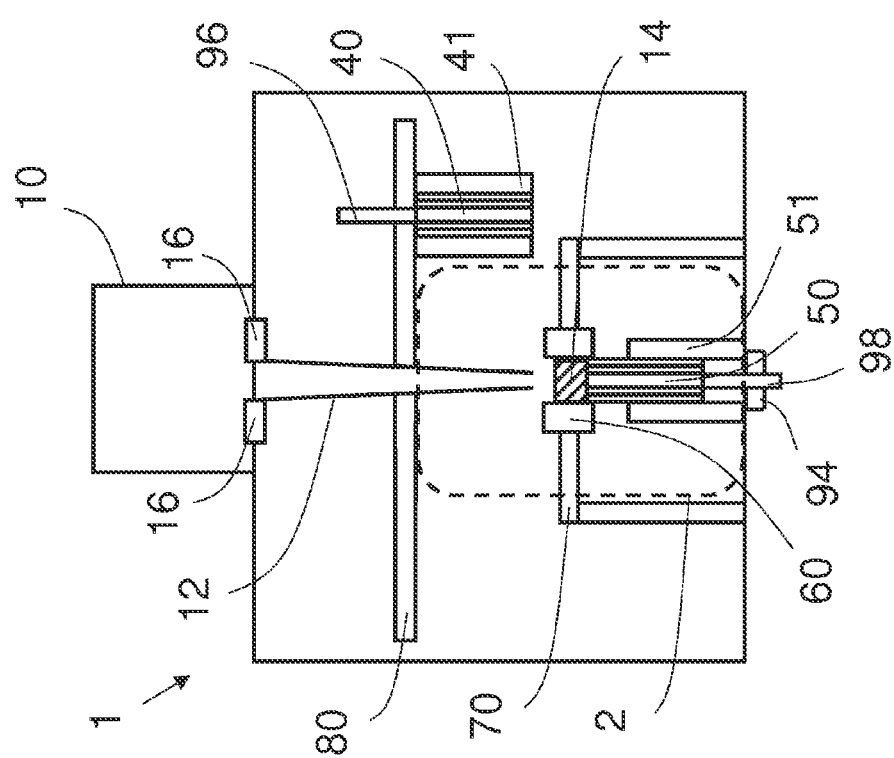
FIG. 4 illustrates a schematically simplified cross-sectional view of a press chamber and a material container of a tablet press during pressing of an active substance.

After the die 60 is filled, the first active substance 14 is pressed. This is shown in FIG. 4. For this purpose, the second positioning device 80 is once again actuated by the control system 6 such that the upper punch 40 is arranged above the lower punch 50 and the die 60. Then, the upper punch 40 is extended into the central opening of the die 60 from above by means of the upper piston 96. In this manner, the first active substance 14 is pressed between the pressure faces of the lower punch 50 and the upper punch 40 in order to form a tablet.

After pressing the tablet, both the upper punch 40 and the lower punch 50 move upwards to release the tablet from the die 60. Then, the tablet is pushed down from the lower punch 50, for example by means of a pushing device (not shown) of the transfer device 4, such that it falls through a channel of the transfer device 4 into the tablet container 100.

This method is repeated until the target number 35 of tablets has been produced. After that, the receiving chamber 3 can be opened and the tablet container 100 removed. The tablet container 100 is now filled with the target number 35 of individualized tablets with the target mass 36 of the first active substance 14.

Figure 5:
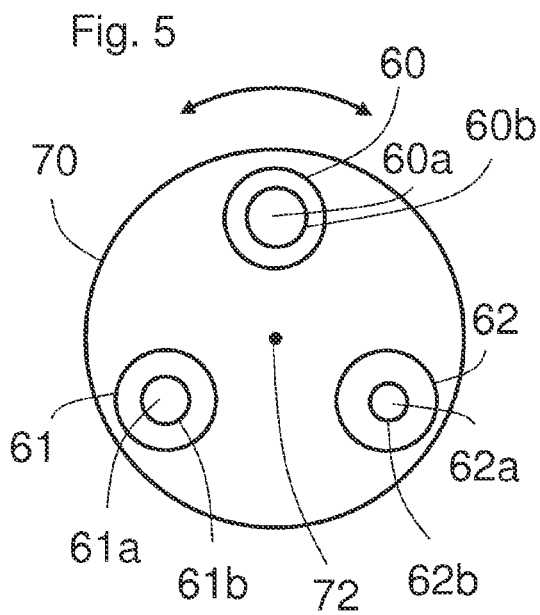
FIG. 5 illustrates a schematically simplified plan view of a first positioning device.

FIG. 5 shows a schematically simplified plan view of an exemplary first positioning device 70. In the embodiment shown, the first positioning device 70 is configured as a first rotary disk with a vertical axis of rotation 72. Three dies 60, 61, 62 are fixed to the first rotary disk. The dies 60, 61, 62 each have a central opening 60a, 61a, 62a with different circular inner circumferences 60b, 61b, 62b. The central openings 60a, 61a, 62a pass through the first rotary disk such that the punches 40, 50 are not blocked by the rotary disk. Which of the dies 60, 61, 62 is arranged above the lower punch 50 can be set by rotating the first rotary disk. In this manner, a target circumference of the produced tablets can be set such that tablets with a wide range of target masses 36 of the first active substance 14 can be produced by means of the tablet press 1.

Alternatively, oval or other shapes can be provided instead of the circular shape of the central openings 60a, 61a, 62a, enabling the shape of the tablets to be adjusted.

Figure 6:
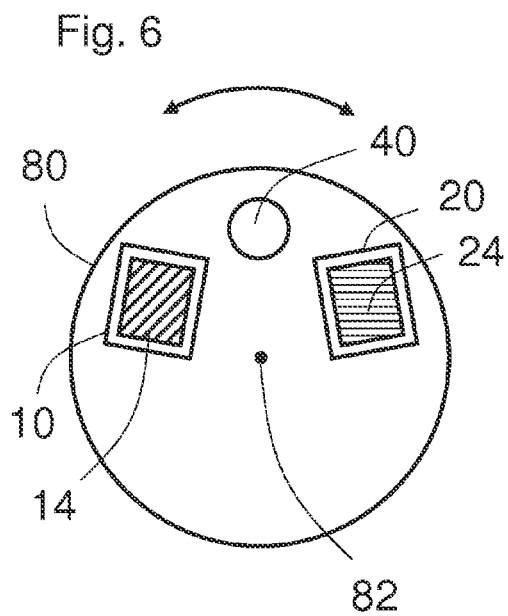
FIG. 6 illustrates a schematically simplified plan view of a second positioning device.

FIG. 6 shows a schematically simplified plan view of the second positioning device 80. In the embodiment shown, the second positioning device 80 is configured as a second rotary disk with a vertical axis of rotation 82. The upper punch 40, the first material container 10, and, in the embodiment shown, a second material container 20 are fixed to the second rotary disk and can be alternately arranged above the lower punch 50 by rotating the second rotary disk.

The second material container 20 is filled with a second active substance 24 for producing a two-layer tablet. For this purpose, after the pressing of the first active substance 14 by means of the second positioning device 80, the second dosing device of the second material container 20 is arranged above the lower punch 50 and the central opening 60a of the die 60 arranged thereon is filled with the second active substance 24. Then, the upper punch 40 is moved above the lower punch 50 and the two-layer tablet is pressed.

Figure 7A:
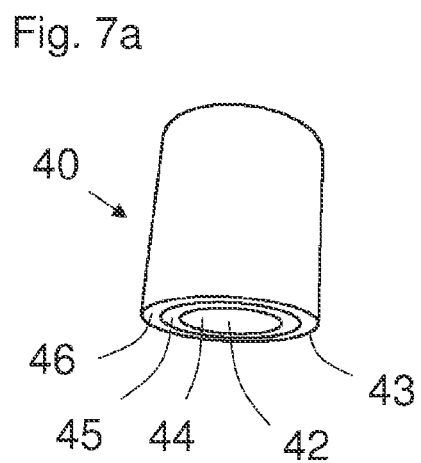
FIG. 7a-d illustrate schematically simplified diagrams of an upper punch with telescoping upper punch shafts arranged inside each other and a lower punch with telescoping lower punch shafts arranged inside each other.
Figure 7B:
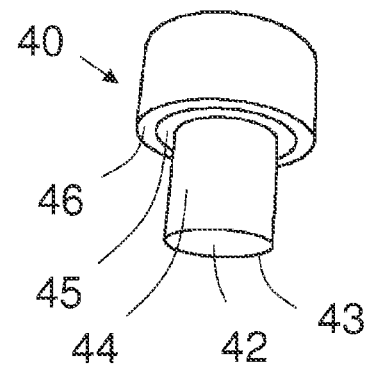

FIGS. 7a and 7b show an embodiment of a telescopable upper punch 40. The upper punch 40 comprises three telescoping upper punch shafts 44, 45, 46 arranged inside each other. In FIG. 7a, all three upper punch shafts 44, 45, 46 are extended together such that the outer circumference 43 of the pressure face 42 of the upper punch 40 corresponds to the outer circumference of the outermost upper punch shaft 46. In FIG. 7b, exclusively the innermost upper punch shaft 44 is extended such that the outer circumference 43 of the pressure face 42 of the upper punch 40 corresponds to the outer circumference of the innermost upper punch shaft 44. The outer circumferences of the upper punch shafts 44, 45, 46 are each complementary in shape to the inner circumferences 60b, 61b, 62b of the dies 60, 61, 62.

Figure 7C:
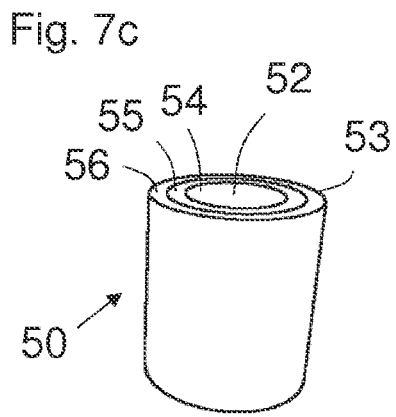
Figure 7D:
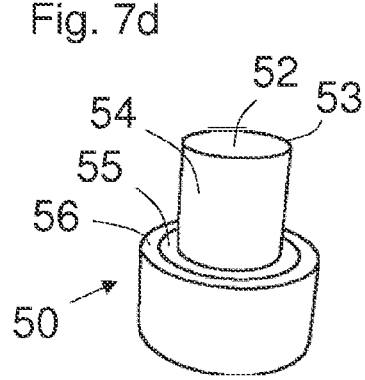

FIGS. 7c and 7d show an embodiment of a telescopable lower punch 50 that is formed as a mirror image to the upper punch 40. Just as with the upper punch 40, the outer circumference 53 of the pressure face 52 of the lower punch 50 can be varied by individually extending the lower punch shafts 54, 55, 56.

In FIG. 8a, a schematically simplified cross-sectional view of a telescopable upper punch 40, a telescopable lower punch 50, and a die 60 are shown during the pressing of a large tablet 101. In this case, the die 60 with the large central opening 60a is used. To press the tablet 101, all upper punch shafts 44, 45, 46 and lower punch shafts 54, 55, 56 are used.

In the embodiment shown, one or more horizontal holes 47 are provided in the upper punch shafts 44, 45, 46, into which holes upper locking pins 48 can be pushed by means of one or more schematically indicated first pushing and pulling devices 49. Analogously, in the embodiment shown, one or more horizontal holes 57 are provided in the lower punch shafts 54, 55, 56, into which holes lower locking pins 58 can be pushed by means of one or more schematically indicated second pushing and pulling devices 59. Since the largest die 60 is used, the locking pins 48, 58 are retracted such that they do not engage in the horizontal holes 47, 57. The pushing direction of the upper piston 96 is represented by an arrow.

FIG. 8b shows a schematically simplified cross-sectional view during the production of a tablet 102 with a medium size. For this purpose, the die 61 is used that has the central opening 61a with the medium size. The locking pins 48, 58 are partially inserted into the holes 47, 57 such that the outermost punch shafts 46, 56 are vertically fixed and only the middle and the inner punch shafts 44, 45, 54, 55 are extended. In this manner, the outer circumferences 43, 53, of the pressure faces 42, 52 are adapted to the inner circumference 61b of the die 61.

FIG. 8c shows a schematically simplified cross-sectional view during the production of a small tablet 103. For this purpose, the die 62 is used that has the smallest central opening 62a. The locking pins 48, 58 are fully inserted into the holes 47, 57 such that the outermost and the middle punch shafts 45, 46, 55, 56 are vertically fixed and only the inner punch shafts 44, 45, 54, 55 are extended. In this manner, the outer circumferences 43, 53, of the pressure faces 42, 52 are adapted to the inner circumference 62b of the die 62.

Figure 9A:
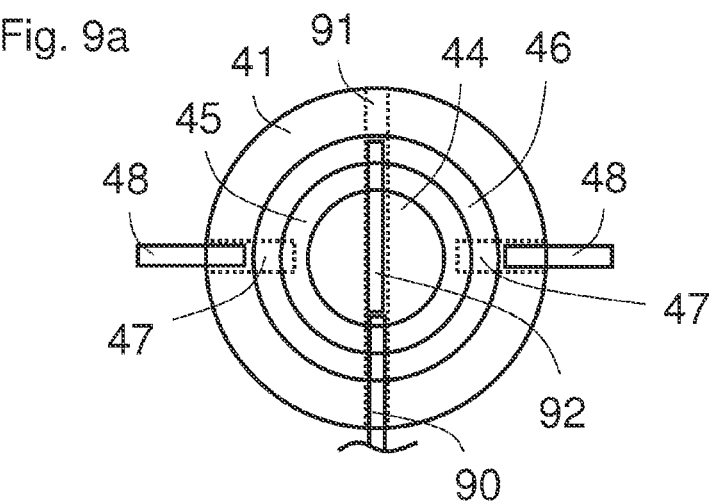
FIG. 9a-c illustrates schematically simplified plan views of an upper punch during the pressing process of tablets with different active substance quantities.

FIG. 9a shows a schematically simplified plan view of FIG. 8a with an additional representation of the upper punch carrier 41 as the outermost ring. A further horizontal hole 91 is provided perpendicularly to the holes 47. A coupling pin 92 is guided in the hole 91 and is inserted into and retracted from the hole 91 by means of a third pushing and pulling device 90.

In the embodiment shown in FIGS. 8a, 8b, 8c, 9a, 9b, 9c, the upper piston 96 drives exclusively the inner upper punch shaft 44 directly, while the lower piston 98 drives exclusively the inner lower punch shaft 54 directly. By means of the coupling pin 92, the upper punch shafts 44, 45, 46 are coupled with each other if necessary, such that they are moved up and down synchronously. This is provided analogously for the lower punch 50. In FIG. 9a, the coupling pin 92 couples all three upper punch shafts 44, 45, 46 with each other such that they are vertically extended together. A vertical groove is provided in the upper punch carrier 41 so that the third pushing and pulling device 90 does not block in the upper punch carrier 41.

Figure 9B:
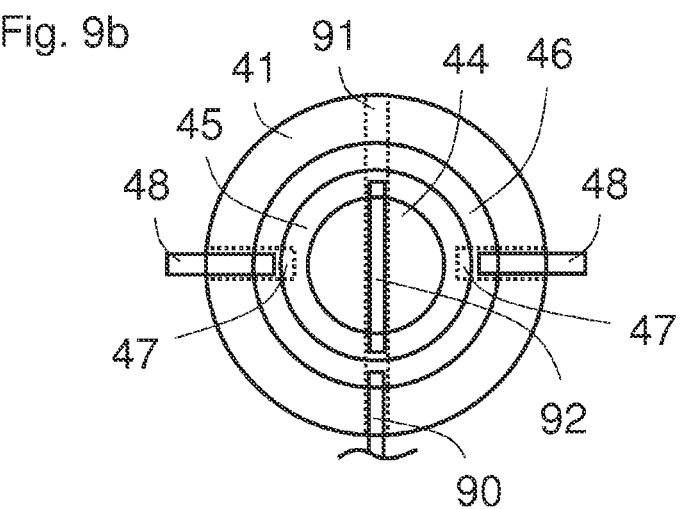

FIG. 9b shows a schematically simplified plan view of FIG. 8b.

The coupling pin 92 couples only the inner upper punch shaft 44 with the middle upper punch shaft 45, while the outer upper punch shaft 46 is vertically fixed.

Figure 9C:
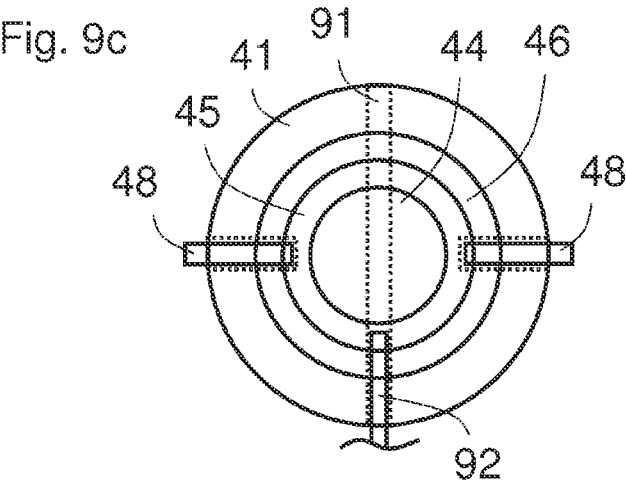

FIG. 9c shows a schematically simplified plan view of FIG. 8c. The coupling pin 92 is inserted such that only the inner upper punch shaft 44 is extended, while the middle upper punch shaft 45 and the outer upper punch shaft 46 are vertically fixed.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

1 Tablet press
2 Press chamber
3 Receiving chamber
4 Transfer device
6 Control system
10 First material container
12 First dosing device
14 First active substance
16 Scale
20 Second material container
24 Second active substance
30 Input device
31 Data display
32, 33, 34 Input means
35 Target number
36 Target mass
37 Second-layer target mass
40 Upper punch
41 Upper punch carrier
42 Pressure face
43 Outer circumference
44, 45, 46 Upper punch shafts
47 Horizontal hole
48 Upper locking pin
49 First pushing and pulling device
50 Lower punch
51 Lower punch carrier
52 Pressure face
53 Outer circumference
54, 55, 56 Lower punch shafts
57 Horizontal hole
58 Lower locking pin
59 Second pushing and pulling device
60, 61, 62 Die
60a, 61a, 62a Central opening
60b, 61b, 62b Inner circumference
70 First positioning device
72 Axis of rotation
80 Second positioning device
82 Axis of rotation
90 Third pushing and pulling device
91 Horizontal hole
92 Coupling pin
94 Pressure measuring device
96 Upper piston
98 Lower piston
100 Tablet container
101, 102, 103 Tablet

What is claimed is:

1. A method for automatically producing a specifiable number of individualized tablets with a specifiable quantity of a first active substance using a tablet press, the method comprising:

inputting a target number which indicates the number of tablets to be produced and a target mass which indicates the quantity of the first active substance per tablet into an input device of the tablet press, transmitting the target number and the target mass from the input device to a controller configured to control the tablet press, wherein the controller controls a first dosing device of a first material container, a vertically extendable upper punch, and a vertically extendable lower punch, wherein the lower punch comprises only a single lower punch, filling a quantity of the first active substance which corresponds to the target mass from the first material container into a central opening of a die using the first dosing device, wherein a pressure face of the lower punch, an outer circumference of which corresponds to an inner circumference of the central opening, closes the central opening from below, selectively moving the upper punch and the first dosing device in a horizontal direction within the tablet press to move the upper punch and the first dosing device above the central opening of the die disposed above the single lower punch while the die and the single lower punch remain stationary in the tablet press and fixed in the horizontal direction;

pressing the first active substance by vertically extending a pressure face of the upper punch, an outer circumference of which corresponds to the inner circumference of the central opening, into the central opening from above, releasing a pressed tablet from the die by retracting the pressure face of the upper punch and vertically extending a pressure face of the lower punch through the central opening from below, and repeating the filling of the quantity of the first active substance, the pressing of the first active substance, and the releasing of the pressed tablet until the number of pressed tablets corresponds to the target number.

2. The method according to claim 1, wherein the controller is configured to:
calculate a filling volume and a target circumference, based on the target mass of the first active substance,
select a target die from at least two dies arranged in the tablet press with different inner circumferences, the inner circumference of the central opening of the target die corresponding to the target circumference, and
actuate a first positioning device such that the target die is arranged above the lower punch.

3. The method according to claim 2, wherein the first positioning device is a first rotary disk with a vertical axis of rotation arranged between the upper punch and the lower punch, on which the at least two dies are arranged in the tablet press are arranged.

4. The method of claim 2, wherein the controller is further configured to calculate the bulk density of the first active substance.

5. The method according to claim 1, wherein the outer circumference of the pressure face of the upper punch for pressing the first active substance is adapted to the inner circumference of the die in that a number of vertically telescoping upper punch shafts of the upper punch arranged inside each other are extended downwards, wherein the outer circumference of the outer extended upper punch shaft corresponds to the inner circumference of the die.

6. The method according to claim 1, wherein the outer circumference of the pressure face of the lower punch is adapted to the inner circumference of the die before the filling of the quantity of the first active substance in that a number of vertically telescoping lower punch shafts of the lower punch arranged inside each other are extended upwards, wherein the outer circumference of the outer extended lower punch shaft corresponds to the inner circumference of the die.

7. The method according to claim 1, wherein the mass of the first active substance filled into the central opening is measured such that, during the filling, the total mass of the first material container is determined by a scale and from this the quantity of the first active substance taken from the first material container is calculated.

8. The method according to claim 1, wherein the first dosing device is arranged vertically above the central opening by a second positioning device during the filling of the quantity of the first active substance, wherein the upper punch arranged vertically above the central opening by the second positioning device after the filling of the quantity of the first active substance and before the pressing of the first active substance.

9. The method according to claim 6, further comprising:
inputting a second-layer target mass into the input device and transmitting a second-layer target mass to the controller, wherein the second-layer target mass indicates a quantity of a second active substance for a second layer of the tablet,
positioning a second dosing device of a second material container above the central opening by the second positioning device,
filling a quantity of the second active substance that corresponds to the second-layer target mass into the central opening by the second dosing device,
positioning the upper punch above the central opening by the second positioning device, and
pressing the second active substance by vertically extending the pressure face of the upper punch into the central opening from above,
wherein, the positioning of the second dosing device, the filling of the quantity of the second active substance, the positioning of the upper punch and the pressing of the second active substance are carried out after pressing the first active substance and before dispensing the pressed tablet.

10. A tablet press for automatically producing a specifiable number of individualized tablets with a specifiable quantity of a first active substance, the tablet press comprising:
a press chamber,
a receiving chamber for receiving a tablet container,
a first material container that can be filled with the first active substance and has a first dosing device,
a controller, and
an input device,
wherein the press chamber has a vertically extendable upper punch, a vertically extendable lower punch, and at least one die,
the input device for inputting a target number that indicates the number of tablets to be produced and a target mass that indicates the quantity of the first active substance per tablet,
the input device is configured to transmit the target number and the target mass to the controller, and
the controller is configured to actuate the first dosing device, the upper punch, and the lower punch such that a quantity of the first active substance that corresponds to the target mass is filled into a central opening of the die and pressed by the upper punch and the lower punch in order to form a tablet, and to repeat actuation of the first dosing device, the upper punch and the lower punch until the target number of tablets are produced;
wherein the lower punch comprises only a single lower punch, and further comprising a first positioning device for selectively moving the upper punch and the first dosing device above the central opening of the die disposed above the single lower punch;

wherein the first positioning device is configured to move the upper punch and the first dosing device in a horizontal direction within the tablet press, and the die and the single lower punch remain stationary in the tablet press and fixed in the horizontal direction.

11. The tablet press according to claim 10, wherein the tablet press comprises at least two dies, the central openings of which have different inner circumferences, wherein the controller is configured to calculate a filling volume and a target circumference, based on the target mass of the first active substance, to select a target die from the at least two dies, the inner circumference of its central opening corresponding to the target circumference, and to actuate a second positioning device such that the target die is arranged above the lower punch.

12. The tablet press according to claim 11, wherein in particular the second positioning device is a first rotary disk with a vertical axis of rotation arranged between the upper punch and the lower punch, on which the at least two dies are arranged.

13. The tablet press according to claim 10, wherein the upper punch comprises at least two vertically telescoping upper punch shafts arranged inside each other, an outer circumference of a pressure face of the upper punch being adapted to the inner circumference of the central opening of the at least one die by individually extending the upper punch shafts.

14. The tablet press according to claim 10, wherein the lower punch comprises at least two vertically telescoping lower punch shafts arranged inside each other, an outer circumference of a pressure face of the lower punch being adapted to the inner circumference of the central opening of the at least one die by individually extending the lower punch shafts.

15. The tablet press according to claim 13, wherein the press chamber comprises a pushing and pulling device having at least one upper locking pin being configured to be pushed into a horizontal hole in side walls of the upper punch shafts to vertically fix a definable number of the upper punch shafts.

16. The tablet press according to claim 14, wherein the press chamber comprises a pushing and pulling device having at least one lower locking pin being configured to be pushed into a horizontal hole in side walls of the lower punch shafts to vertically fix a definable number of the lower punch shafts.

17. The tablet press according to claim 10, wherein the first material container is coupled with a scale for measuring the total mass of the first material container.

18. The tablet press according to claim 10, wherein the first positioning device further accommodates a second dosing device of a second material container.

19. The tablet press according to claim 10, wherein one or more of the lower punch and the upper punch are coupled with a pressure measuring device for measuring a pressure acting on one or more of the lower punch and the upper punch.

* * * * *